United States Patent [19]

Brock et al.

[11] 4,394,450
[45] Jul. 19, 1983

[54] METHOD FOR PURIFICATION OF URICASE

[75] Inventors: David A. Brock; Surendra K. Gupta, both of Elkhart, Ind.

[73] Assignee: Miles Laboratories, Inc., Elkhart, Ind.

[21] Appl. No.: 353,484

[22] Filed: Mar. 1, 1982

[51] Int. Cl.$^3$ .......................... C12N 9/06; C12Q 1/62
[52] U.S. Cl. ...................... 435/191; 435/10; 435/814
[58] Field of Search .................. 435/191, 10

[56] References Cited

U.S. PATENT DOCUMENTS

| 2,878,161 | 3/1959 | Robbins et al. | 435/191 |
| 3,431,176 | 3/1969 | Fukumoto et al. | 435/171 |
| 3,475,276 | 10/1969 | Kano | 435/191 |
| 3,620,923 | 11/1971 | Laboureur et al. | 435/191 |
| 3,669,843 | 6/1972 | Aunstrup et al. | 435/191 |
| 3,810,820 | 5/1974 | Laboureur et al. | 435/191 |
| 4,062,731 | 12/1977 | Snoke et al. | 435/191 |
| 4,064,010 | 12/1977 | Harris | 435/191 |

OTHER PUBLICATIONS

Watanabe et al, Analytical Biochemistry, vol. 89, pp. 343–347, (1978).
J. Biol, Chem., 216:625–641, 1955. "Studies on Uricase", by H. R. Mahler, G. Hubscher and H. Baum.

Primary Examiner—Lionel M. Shapiro
Attorney, Agent, or Firm—James D. McNeil

[57] ABSTRACT

A method is provided for purifying uricase by decreasing the amount of active catalase present. The method involves adjusting the pH of a catalase-containing uricase preparation to a pH in the range of about 11 to 13 to inactivate the catalase and recovering a uricase preparation substantially free of active catalase.

7 Claims, No Drawings

METHOD FOR PURIFICATION OF URICASE

BACKGROUND OF THE INVENTION

1. Field of the Invention

This invention relates to the purification of uricase and especially to the inactivation of catalase in a uricase preparation.

In human metabolism, there is a constant endogenous conversion of ingested nucleoproteins to substances such as purines. Purines, by a catabolic process, undergo further deamination and partial oxidation to uric acid, which, in humans, is normally excreted in the urine. This results in a nominal concentration of uric acid in the blood and urine of humans at all times. In pathological conditions, for example, renal insufficiency, uremia, gout and leukemia, there is an abnormal increase in the amount of uric acid found in urine or blood serum.

Medical science has recognized the usefulness of a test for measuring the amount of uric acid in the blood serum or urine as an aid in diagnosing the above-described conditions. One such test method involves the use of uricase to decompose uric acid by catalyzing the oxidation of uric acid to allantoin and hydrogen peroxide and measuring the amount of hydrogen peroxide formed, to determine the amount of uric acid Uricase also can be used in pharmaceutical preparations. Such uricase must be substantially free of contaminants.

Animal organs have heretofore been the principal source of uricase. Difficulties in extraction and purification of uricase from such sources, along with the uncertainty of supply of such animal organs have encouraged the development of uricase production from microorganisms.

In the production of an enzyme such as uricase, whether by extraction from animal tissue or by fermentation of a microorganism, the desired enzyme is generally found in a liquid medium with various other macromolecules such as proteins, other enzymes and/or other undesirable material. Various methods of purifying uricase are well-known and include organic solvent precipitation, ammonium sulfate fractionation, ion-exchange chromatography and gel filtration. Generally, even after such purification steps have been taken, the resulting uricase enzyme is not pure, but contains some amounts of protein impurities.

The principal contaminant of uricase is the enzyme catalase. Catalase is an undesirable impurity, whether the uricase is to be used as a pharmaceutical preparation or used for the quantitative analysis of uric acid in a detection system which includes hydrogen peroxide. Catalase causes the decomposition of hydrogen peroxide; thus the presence in uricase of catalase in an active form will produce a misleadingly low value of uric acid in the biological fluid measured.

2. Description of the Prior Art

U.S. Pat. No. 2,878,161 describes obtaining uricase from uricase-bearing tissue such as liver tissue derived from hogs, cattle or sheep.

The production of uricase from various microorganisms, including bacteria, fungi, and yeast is described in U.S. Pat. Nos. 3,431,176; 3,475,276; 3,620,923; 3,669,843; and 4,062,731.

U.S. Pat. No. 3,810,820 describes the production of uricase using bacteria and fungi belonging to various species. The mycelial extract obtained from the culture medium, containing uricase together with numerous proteins, is purified by a series of precipitations from aqueous medium using organic liquids miscible with water or aqueous solutions containing ammonium sulfate. The patentee suggests the use of adsorption upon hydroxyapatite, bentonite and alumina and subsequent extraction, followed by elution using saline solutions. Purification can be carried still further by subjecting the thus-obtained products to chromatography.

U.S. Pat. No. 4,064,010 describes a method for purification of uricase, and specifically the removal of catalase from uricase. The patentees refer to the use of ammonium sulfate as a purification technique and claim the process of separating catalase present by passing the catalase-containing uricase through a chromatographic column of cyanogen bromide-activated polysaccharide material having a hydrophobic ligand attached.

The complicated and expensive prior art methods indicate that there is a need for a simple and economical method for purification of uricase.

SUMMARY OF THE INVENTION

The present invention relates to a convenient and economical method of purifying uricase by inactivating catalase present. The method involves the steps of adjusting the pH of a catalase-containing uricase preparation to a pH in the range of about 11 to 13 to inactivate the catalase. The uricase preparation can be used with the inactivated catalase present, or alternatively the catalase can be removed and substantially catalase-free uricase recovered.

DETAILED DESCRIPTION OF THE INVENTION

According to the present invention, catalase-containing uricase is adjusted to a pH in the range of about 11 to 13 to inactivate catalase present.

Adjustment of the pH to a range of about 11 to 13 has been found to be a critical limitation. If the pH is below about 11, the catalase is not inactivated. At a pH greater than about 13, the uricase begins to become inactivated. The identity of the base used to adjust the pH is not critical. For example, bases such as sodium or potassium hydroxide are suitable. The inactivated catalase, along with minor amounts of other proteineous materials, can be removed by conventional techniques. Where uricase is obtained by microbial fermentation, the uricase-containing cells are disrupted and impurities removed by centrifugation. Where uricase is obtained from uricase-bearing tissue, the uricase can be removed by aqueous extraction with a saline solution.

The following Examples involve obtaining catalase-containing uricase by microbial fermentation. Uricase can be obtained from bacterial, fungi and yeast fermentation as described hereinbefore. It is understood that catalase-containing uricase can also be obtained from appropriate animal tissue as described hereinbefore.

In one embodiment of the present invention the catalase and uricase-containing microorganisms were first disrupted and the catalase subsequently inactivated by adjusting the pH to a range of about 11 to 13.

In a preferred embodiment of the present invention, the pH of the catalase and uricase-containing microorganisms was adjusted to a pH in the range of about 11 to 13 to inactivate the catalase. The microorganisms were then centrifuged to remove undesired material present. It is theorized that proteinaceous components, including some inactivated catalase, are removed by centrifugation after pH adjustment. The microorganisms were then disrupted to release the uricase. Uricase essentially free of active catalase was recovered by centrifugation.

The cells can be disrupted by ultrasonic techniques, e.g., an ultrasonic probe or by pressure techniques, e.g., a press. Other methods may be used, e.g., the uricase can be extracted by freezing the microorganisms at a temperature about $-15°$ to $-70°$ C., and thawing the microorganisms, or breaking the cells by addition of appropriate lysozymes.

EXAMPLE I

Lyophilized cells of *Bacillus fastidiosus* (SMG 83), available from the Culter Collection Institute für Mikrobiologie, Güttingen, Germany, were grown in a medium containing per liter: uric acid 8 g; Brain Heart infusion, 4 g; potassium phosphate monobasic, 1.5 g; sodium phosphate dibasic, 3.6 g; $MgSO_4.7H_2O$, 0.2 g; $CaCl_2$, 0.02 g; ferric ammonium citrate, 1.2 mg; $MgCl_2.4H_2O$, 1 mg. The bacterial cells were grown at 37° C. four about 12 to 16 hours and separated from the fermentation mixture by centrifugation.

The catalase and uricase produced by microbial fermentation are present inside the microorganism cells. The cells can be suspended in a buffer solution of approximately neutral pH. The identity and pH of the buffer is not critical; for example, a phosphate or borate buffer at a pH of about 7 to 9 is suitable.

The centrifuged cells were suspended in 0.005 M borate buffer at a pH of about 9.0 and the cells disrupted at about 15,000 psi using a French press commercially available from American Instrument Company, Silver Springs, Md. A crude extract containing active uricase and active catalase was obtained by removing the cell debris by centrifugation at 10,000 g×20 minutes.

The pH of the crude extract was then adjusted to pH 12.0 using 1 M KOH solution. After 10 to 20 minutes, the pH was adjusted back to 8.0 using a conventional acidic agent, such as acetic acid, and the activity again determined. The uricase and catalase activity of the crude extract was determined as described below.

Uricase activity was assayed spectrophotometrically by following the disappearance of uric acid at 293 nm on a Gilford 250 spectrophotometer, using a modification of the procedure described by Mahler, et. al., in *J. Bio. Chem.*, 216:625 (1955).

A 0.02 M sodium tetraborate buffer, (pH 9.1) was prepared by dissolving 3.81 grams of $Na_2B_2O_7.10H_2O$ (molecular weight 381.36) in distilled water and adjusting the volume to 500 ml.

The uric acid substrate was prepared by weighing a 50 mg portion of uric acid (molecular weight 168.0) and dissolving it in 0.02 M borate buffer to a final volume of 50 ml to produce a solution containing 1 mg uric acid/ml solution. A 1 ml aliquot of this solution was removed and added to 99 ml of 0.02 M borate buffer to give 100 ml of substrate solution. Fifty μl of crude extract was assayed after diluting it 1:20 in 0.2 M borate buffer.

The following was introduced into a 10 mm quartz cuvette: 3.0 ml of the uric acid substrate solution and 0.05 ml of the crude extract diluted as described above. The rate decrease in absorbance at 293 nm at 25° C. was recorded and the enzyme activity calculated as Units/ml uricase, where a Unit is defined as the amount of uricase which catalyzes the conversion of one μmole of urate per minute at 25° C. The following equation was used:

Uricase activity $(U)$/ml =

$$\frac{\Delta Absorbance\ at\ 293/min \times ml\ (enzyme + substrate) \times dilution}{(millimolar\ extinction\ coefficient\ of\ uric\ acid)^* \times ml\ enzyme}$$

*12.6

Catalase activity was assayed spectrophotometrically by measuring the decomposition of hydrogen peroxide to water and oxygen by catalase.

A 0.05 M potassium phosphate buffer solution (pH 7.0) was produced by dissolving 3.4 grams of potassium monophosphate, (molecular weight 136) in 400 ml distilled water and adjusting the pH to 7.0 by adding KOH and thereafter adjusting the volume to 500 ml.

The 0.05 M potassium phosphate buffer was used to dilute 30 percent hydrogen peroxide to a pH of 7.0, having an absorbance at 240 nm of between 0.5 and 0.55.

The following was introduced into 10 nm quartz cuvette cells:

|  | Test | Control |
|---|---|---|
| Buffer | 0 | 3.0 ml |
| Substrate | 2.9 ml | 0 |
| Crude Extract | 0.1 ml | 0 |

The catalase activity was calculated as follows:

Catalase activity $(U)$/ml =

$$\frac{\Delta Absorbance\ 240/min \times ml\ (enzyme + substrate) \times dilution}{(millimolar\ extinction\ coefficient\ hydrogen\ peroxide)^* \times ml\ enzyme}$$

*0.043

The specific activity is defined as Unit/ml activity of an enzyme divided by protein concentration in mg/ml. The protein concentration was determined by the method of Lowry, et. al., *J. Biol. Chem.*, 193:265 (1951).

The uricase activity value obtained was used to determine the uricase specific activity as described above.

The uricase and catalase activity and uricase specific activity obtained with and without the pH adjustment of the present invention, are shown in Table I below.

TABLE I

|  |  | Units/ml | | Sp. Activity Uricase |
|---|---|---|---|---|
|  |  | Uricase | Catalase | U/mg |
| (1) | Crude extract (without pH adjustment) | 3.2 | 5,262 | 0.5 |
| (2) | Crude extract after pH adjustment to 12.0 | 2.9 | 13 | 0.4 |

As indicated earlier, catalase present in uricase is detrimental if the catalase is present in an active form. In the above procedure, the experimental results indicate that the activity of the catalase was reduced by more than 99 percent, from 5,262 U to 13 U, on a ml basis. The specific uricase activity remained relatively constant, because essentially no protein, including catalase, was removed from the extract.

A second procedure was carried out to attempt to increase the uricase specific activity by removing some of the inactivated catalase. The procedure described below involved first adjusting the pH of catalase and uricase-containing microbial cells and then centrifuging the cells to remove some of the proteinaceous components.

EXAMPLE II

Cells of *B. fastidiosus* (SMG-83) were grown as described in Example I and separated from the fermentation mixture by centrifugation.

The centrifuged cells were resuspended in 0.1 M phosphate buffer at a pH of about 7.0. Following suspension of the cells, the pH of the suspension was adjusted to about 12.1 by addition of potassium hydroxide to inactivate the catalase. The cell suspension was then stirred at room temperature for about 20 minutes. The cells were centrifuged at about 10,000 g for 20 minutes, washed and resuspended in 0.005 M borate buffer.

The bacteria cells were lysed by disrupting the cells by the procedure described in Example I, and again centrifuged at about 10,000 g for 20 minutes.

The supernatant obtain was assayed for uricase and enzyme activity by the procedure described in Example I. Uricase and catalase activities obtained are shown in Table II below.

TABLE II

|  | Units/ml | | Sp. Activity Uricase |
|---|---|---|---|
|  | Uricase | Catalase | U/mg |
| (1) Cells with no pH adjustment | 1.1 | 454 | 1.9 |
| (2) Cells with pH adjustment | 0.9 | 0.5 | 6.2 |

As can be seen by the results summarized in Table II, pH adjustment to 12.1 of the uricase cell suspension followed by centrifugation, reduced the catalase activity by more than 99 percent. As indicated earlier, centrifugation of the cells after pH adjustment appears to remove proteinaceous components including some inactivated catalase, which increases the specific activity of uricase, between 3-4 fold.

The uricase preparation recovered had a high uricase activity, approximately 6 Units (U) per milligram.

What is claimed is:

1. A method for purifying uricase by decreasing the amount of active catalase present which comprises adjusting the pH of a catalase-containing uricase preparation to a pH in the range of about 11 to 13 to inactivate said catalase, and recovering therefrom a uricase preparation substantially free of active catalase.

2. A method as claimed in claim 1, wherein the uricase is obtained from microorganisms.

3. A method as claimed in claim 1, wherein the uricase is obtained from uricase-bearing tissue.

4. A method as claimed in claim 1, wherein the inactivated catalase is removed from the uricase preparation.

5. A method as claimed in claim 4, wherein the inactivated catalase is removed by centrifuging the uricase preparation after said pH adjustment.

6. A method for purifying uricase by decreasing the amount of active catalase present which comprises the steps of cultivating uricase-producing microorganism cells to produce uricase and catalase, adjusting the pH of the cells to a pH in the range of about 11 to 13 to inactivate said catalase, centrifuging said cells, disrupting said cells and recovering therefrom a uricase preparation substantially free of active catalase.

7. A method for purifying uricase by decreasing the amount of active catalase present which comprises the steps of cultivating uricase-producing microorganism cells to produce uricase and catalase, disrupting the cells, adjusting the pH of the cells to a pH in the range of about 11 to 13 to inactivate said catalase, and recovering therefrom a uricase preparation substantially free of active catalase.

* * * * *